United States Patent [19]

Ritterband

[11] Patent Number: 4,946,776

[45] Date of Patent: Aug. 7, 1990

[54] STABLE CHROMOGENIC SUBSTRATE MIXTURE OF INDOXYL PHOSPHATE AND TETRAZOLIUM SALT, METHOD OF MAKING AND USING SAME IN BIOLOGICAL AND DIAGNOSTIC ASSAYS

[75] Inventor: Menachem Ritterband, Rehovot, Israel

[73] Assignee: Orgenics Ltd., Israel

[21] Appl. No.: 292,578

[22] Filed: Dec. 30, 1988

[30] Foreign Application Priority Data

Jan. 3, 1988 [IL] Israel ......................................... 85018

[51] Int. Cl.$^5$ .............................................. C12Q 1/42
[52] U.S. Cl. ........................................ 435/21; 435/26; 435/29; 435/810; 435/4; 436/164
[58] Field of Search ..................... 435/21, 29, 810, 26, 435/188, 4; 436/164

[56] References Cited

U.S. PATENT DOCUMENTS

4,613,569 9/1986 Geiser et al. ......................... 435/810
4,748,115 5/1988 Steaffens ............................... 435/21

FOREIGN PATENT DOCUMENTS

0228663 7/1987 European Pat. Off. .............. 435/21

*Primary Examiner*—Esther M. Kepplinger
*Assistant Examiner*—Laurie A. Scheiner
*Attorney, Agent, or Firm*—Ostrolenk, Faber, Gerb & Soffen

[57] ABSTRACT

A stable chromogenic substrate mixture of indoxyl phosphate and tetrazolium salt is prepared by dissolving the phosphate in DMF and combining the same with Tris buffer containing magnesium chloride and followed by combination of the same with a DMF solution of tetrazolium salt. The resulting mixture is stored below room temperature in the absence of light.

9 Claims, No Drawings

STABLE CHROMOGENIC SUBSTRATE MIXTURE OF INDOXYL PHOSPHATE AND TETRAZOLIUM SALT, METHOD OF MAKING AND USING SAME IN BIOLOGICAL AND DIAGNOSTIC ASSAYS

BACKGROUND

Chromogenic enzyme substrates or chromogenic substrate mixtures are of wide use and importance in the fields of biology and medicine. Body enzymes are detected and measured in clinical chemistry as part of diagnosis of metabolic and other diseases. Enzymes are utilized as a label in biological assays and assay kits, which are based on receptor and analyte pairs (e.g. see U.S. Pat. Nos. 4,193,983 and 4,391,904). In such instances the chromogenic substrate system generates the signal of the assay.

In some cases the biological system or the design of the assay warrant the generation of an insoluble colored product as the signal. The most frequently used examples of such instances will be histochemistry, dot assays, Western blots, and assay kits based on immunoconcentration devices (U.S. Pat. No. 4,632,901).

One of the most frequently used enzymes in the field of biological assays is alkaline phosphatase (Voller, A. and Bidwell, D. "Enzyme-Linked Immunosorbent Assay", in: Rose, N. R., Friedman, H. and Fahey, J. L. (eds) "Manual of Clinical Laboratory Immunology", 3rd Edition, American Society of Microbiology, Washington, D.C., 1986, pp: 99–109). This enzyme has a multitude of substrates, which produce an insoluble, colored product. Some of these substrates and the method for their utilization are presented in the book "Enzyme Histochemistry - A Laboratory Manual" by Z. Lojda, R. Gossrau and T. H. Schiebler, Springer-Verlag, Berlin Heidelberg New York, 1979. Of special interest is the tetrazolium dye method, which involves 2 reaction steps, both occur in the same solution:

1. Primary reaction (enzyme specific)
Indoxyl phosphate

Indoxyl + Disodium hydrogen phosphate

2. Secondary reaction (reduction of tetrazolium)
Tetrazolium chloride + Indoxyl → Formazan dye + Indigo white + HCl The formazan dye precipitates at the location of the reaction. This method is rapid, sensitive and the formed dye is stable.

For preparation of the reaction mixture the indoxyl phosphate and the tetrazolium salt are dissolved in an appropriate solvent, such as dimethyl formamide and then incorporated in a Tris-(tris(hydroxymethyl)aminomethane) or veronal buffer having a pH of 9–10. The mixture thus formed is not stable and will deteriorate within a few hours by spontaneous precipitation of the formazan dye.

THE INVENTION

The invention is a stable, ready-for-use mixture of indoxyl phosphate and tetrazolium salt, its method of preparation and its use in diagnostic or other biological kits.

DETAILED DESCRIPTION OF THE INVENTION

1. Preparation of a stable mixture of indoxyl phosphate and tetrazolium salt.

Indoxyl phosphate, preferably bromo chloro indoxyl phosphate (BCIP) is dissolved in dimethyl formamide at concentrations of 10–75 mg/ml, preferably 50 mg/ml. The suspension is poured into 0.1M Tris HCl pH 9.0–10.5, preferably pH 9.5, containing 5 mM of magnesium chloride, and stirred vigorously for 10 minutes. Tetrazolium salt, preferably Nitro Blue Tetrazolium Chloride, is dissolved in 70% dimethyl formamide at concentrations 10–100 mg/ml, preferably 75 mg/ml. This suspension is added under vigorous stirring to the BCIP solution. Stirring is continued for preferably 10 minutes. The complete solution is stored in the dark under normal mechanical refrigeration (4°–15° C.), preferably at 4°–8° C. Under these conditions the shelf life is longer than 1 year. The solution can be stored for a few months at room temperature (19°–37° C.). The dark storage is imperative for the stability of the product.

Very often the substrate solution degrades due to contamination with bacteria or residual enzymatic activity in the vessels in which the mixture is prepared or stored. Shelf life is increased when using heat or steam sterilised vessels and sterile disposable pipettes.

2. Use of stable indoxyl-tetrazolium solution in Detection and Demonstration of Enzymatic Activity on Solid Surfaces.

The solid object with alkaline phosphatase on it (a tissue preparation on a slide, a blot or dot on a filter membrane, a dot on plastic) is dipped into the indoxyl-tetrazolium solution for a period of 1–30 minutes (prefereably 5–20 minutes) at 19°–37° C., preferably at room temperature (20°–30° C.). The color develops and precipitates spontaneously at the location of the enzyme. Reaction is stopped by washing the object in water and air drying.

A complete preparation procedure is detailed in Example 1.

EXAMPLE 1 PREPARATION OF A STABLE BCIP-NBT SOLUTION.

Step 1: 0.2 gr of 5-bromo-4-chloro-3-indolyl phosphate, toluidine salt (BCIP, obtainable from Sigma Chemical Co., St. Louis, Mo., USA) is dissolved in 4 ml dimethyl formamide (DMF).

Step 2: The solution obtained in Step 1 is added to 1 liter 0.1M Tris HCl, pH 9.5, containing 5 mM of magnesium chloride, followed by rigorous stirring for about 10 minutes.

Step 3: 300 mg of Nitro Blue Tetrazolium Chloride (NBT; also obtainable from Sigma Chemicals) are dissolved in 4 ml of 70% DMF and added to 1 liter of the BCIP solution obtained in step 2, followed immediately by vigorous stirring. Store cold and dark.

EXAMPLE 2: USE OF THE BCIP-NBT MIXTURE IN A DIAGNOSTIC ASSAY

1. Standard Rubella virus Hemagglutination Antigen, such as obtainable from Wellcome Diagnostics or Behring Diagnostics, is diluted 1:20 in Dulbecco's Phosphate Buffered Saline (PBS). 3–6 microliter drops of the Antigen solution are dried on nitrocellulose or polystyrene sheets. Following drying, the sheets are blocked by dipping in 1% BSA, 10% Horse Serum (e.g. obtained from GIBCO) in PBS and washed in water.

2. Human serum specimens are diluted in a diluent, consisting of 1% BSA, 10% Horse serum and 0.85% sodium chloride to final dilution of at least 1:15. Pieces of the polystyrene or nitrocellulose sheets with Rubella antigen spots are dipped into the diluted specimens and incubated for 10-30 minutes at room temperature (about 20° C.).

3. Following a wash in 0.05% detergent solution (Tween-20 or Brij 35T), the above treated sheets are dipped into a solution of an alkaline phosphatase anti human anti IgG Fc conjugate (obtainable from various suppliers such as Sigma Chemicals, KPL, BioMakor) diluted 1:100-1:500 in specimen diluent. Incubation proceeds for 10-30 minutes at room temperature.

4. At the end of the incubation period, the sheets are washed thoroughly in running water and dipped into the BCIP-NBT mixture for a period of 5-20 minutes at room temperature. Gray purple spots appear at the location of the antigen spots, which were reacted with positive specimens.

The foregoing description is only illustrative of said compositions, their methods of preparation and uses. Accordingly, the scope of the invention is to be considered limited only by the appended claims.

What is claimed is:

1. A method of preparing a stable chromogenic substrate mixture of indoxyl phosphate and tetrazolium salt comprising the steps of
    (a) dissolving indoxyl phosphate in dimethyl formamide at a concentration of 10-75 mg/ml; and
    (b) combining said dissolved indoxyl phosphate with tris(hydroxymethyl)aminomethane buffer pH 9.0-10.5 containing magnesium chloride with stirring; and
    (c) dissolving tetrazolium salt in 70% dimethyl formamide at a concentration of 10-100 mg/ml.
    (d) mixing said solution (b) with solution (c) with stirring; and
    (e) storing said mixture below about 20° to 30° C. and in the absence of light.

2. The method of claim 1, wherein said indoxyl phosphate is bromo-chloro indoxyl phosphate.

3. The method of claim 1, wherein said tetrazolium salt is Nitro Blue tetrazolium chloride.

4. A chromogenic enzyme substrate characterized in that it is a stable chromogenic substrate mixture of indoxyl phosphate and tetrazolium salt prepared in accordance with claim 1.

5. In the method of detecting enzymatic activity in biological and diagnostic assays comprising the steps of:
    (a) dipping a solid surface having an enzyme bound thereto into a chromogenic substrate mixture at room temperature until color spots develop;
    (b) washing and air-drying said solution (a) from said solid surface and
    (c) measuring said enzymatic activity
    the improvement which comprises employing the stable substrate of claim 4 as said substrate.

6. The method of claim 1, wherein said buffer contains 0.1M tris(hydroxymethyl)aminomethane and 5 mM of magnesium chloride.

7. The method of claim 6, wherein said indoxyl phosphate is bromo-chloro indoxyl phosphate.

8. The method of claim 7, wherein said tetrazolium salt is Nitro Blue tetrazolium chloride.

9. The method of claim 8, wherein said buffer is pH 9.5, the amount of said phosphate is 50 mg/ml and the amount of said tetrazolium chloride is 75 mg/ml.

* * * * *